United States Patent [19]
Green et al.

[11] Patent Number: 5,931,798
[45] Date of Patent: Aug. 3, 1999

[54] ORTHOPEDIC CASTING TAPE HAVING ALTERNATING THICK AND THIN PORTIONS

[75] Inventors: Richard Green, Livingston, N.J.; James V. Snipes, Clemmons, N.C.

[73] Assignees: Carolina Narrow Fabric Company, Winston-Salem, N.C.; Johnson & Johnson Orthopaedics, Inc., New Brunswick, N.J.

[21] Appl. No.: 08/058,592

[22] Filed: May 7, 1993

[51] Int. Cl.[6] ....................................................... A61F 5/01
[52] U.S. Cl. ................................................... 602/6; 66/193
[58] Field of Search ............................. 66/196, 193, 194, 66/195, 190, 192; 602/5, 6, 8

[56] References Cited

U.S. PATENT DOCUMENTS

| | | | |
|---|---|---|---|
| 3,077,758 | 2/1963 | Siciliano | 66/192 |
| 3,625,029 | 12/1971 | Safrit et al. | 66/192 |
| 3,787,272 | 1/1974 | Nisbet et al. | 66/195 |
| 3,881,473 | 5/1975 | Corvi et al. | 66/195 |
| 3,882,857 | 5/1975 | Woodall, Jr. | |
| 4,103,485 | 8/1978 | Brües | 66/192 |
| 4,248,064 | 2/1981 | Odham | 66/192 |
| 4,320,634 | 3/1982 | Hashimoto et al. | |
| 4,323,061 | 4/1982 | Usukura | 66/195 |
| 4,333,321 | 6/1982 | Schneider et al. | 66/192 |
| 4,467,625 | 8/1984 | Kurz | 66/190 |
| 4,502,479 | 3/1985 | Garwood et al. | |
| 4,609,578 | 9/1986 | Reed | |
| 4,668,563 | 5/1987 | Buese et al. | |
| 4,745,912 | 5/1988 | McMurray | |
| 4,753,088 | 6/1988 | Harrsion et al. | 66/192 |
| 4,898,159 | 2/1990 | Buese et al. | 602/8 |
| 5,014,403 | 5/1991 | Buese | 28/170 |
| 5,088,484 | 2/1992 | Freeman et al. | |

OTHER PUBLICATIONS

A. Reisfeld; "Fundamentals of Raschel Knitting", Published by National Knitted Outerwear Associated; pp. 1–8.

*Primary Examiner*—Michael O'Neill
*Attorney, Agent, or Firm*—Alston & Bird LLP

[57] ABSTRACT

The invention is directed to orthopedic casting tapes including the combination of a knit tape and a hardenable liquid resin coated onto the knit tape. The knit tape includes alternating thick and thin portions extending transversely across the tape. Such casting tapes have been found to be capable of improving cast strength.

23 Claims, 3 Drawing Sheets

ORTHOPEDIC CASTING TAPE HAVING ALTERNATING THICK AND THIN PORTIONS

FIELD OF THE INVENTION

The invention relates to an improved orthopedic casting tape and to orthopedic casts. More specifically, the invention relates to orthopedic casting tapes having excellent conformability and strength properties.

BACKGROUND OF THE INVENTION

Polymeric casting materials have gained widespread commercial acceptance during the past decade. As compared to Plaster of Paris casts, the polymeric or so-called "synthetic" casting materials have advantages of being lightweight and strong. Synthetic casting materials are also porous in the hardened state so that the cast is breathable. Typically, orthopedic synthetic casts are made from a curable resin-impregnated narrow fabric or casting tape. The fabric, which is preferably knit, can be formed of glass fibers, and/or synthetic fibers, such as polyester, nylon, polyolefins, and the like.

Water hardenable polyurethane prepolymers disclosed in Yoon, U.S. Pat. No. 4,433,680, constitute a particularly desirable hardenable resin for use in synthetic casting materials. These casting materials employ a water activatable polyurethane prepolymer which contains a dimorpholinodiethylether catalyst. These compositions have a long shelf life during which the polyurethane polymer remains in a liquid state. When the bandage is to be used, it is removed from a sealed package and placed in water for a few seconds. It is removed from the water and applied to the patient, usually over a tubular, knitted fabric and a padding. The bandage will set rapidly to a condition where it is capable of immobilizing a fracture.

The properties and functionality exhibited by the finished cast result both from the fabric and from the resin employed in constructing the casting tape. Ideally, the final cast has both a high degree of strength and a high porosity, resulting in a breathable cast. It is also important that the final cast conforms uniformly to the irregular surfaces of the patient's body. This is necessary in order that the damaged portion of the body be fully supported during healing. In addition high conformability minimizes the formation of wrinkles and puckers which can result in pressure areas in the cast that can cause patient discomfort and interfere with healing. Conformability is also important for ease of application. Surgeons and casting technicians can provide more cost efficient services when applying conformable fabrics which easily adapt to body contours without generating tucks and bulges which, as discussed previously are objectionable both from a patient comfort and healing standpoint, and therefore must be removed or minimized during the wrapping process.

High modulus fibers, such as glass fibers, are widely used in synthetic casting materials due to their ability to impart high strength characteristics to the final casting bandage. In addition, the use of fibers having a high modulus or stiffness minimizes the tendency of the fabric to become compressed and flattened while being coated and wrapped. This in turn, preserves both the shape and the mesh structure of the fabric resulting in a porous cast with a high degree of breathability.

Although the high modulus fibers have a beneficial impact on cast strength, the high modulus fibers also provide stiffer fabrics which typically do not conform well to complex surfaces. In addition, the need for high strength dictates the use of relatively high density fabrics, which decreases still further the ability of the fabric to conform uniformly to irregular body surfaces.

The ability of a fabric to process well during a liquid resin coating operation is also important. Thus, the fabric must remain flat as it is fed to and passed between coating rollers which apply a resin coating to the fabric. Moreover, the resin distribution along the fabric must be uniform to ensure uniformity in the final cast.

Buese et al., U.S. Pat. No. 4,668,563 discloses high modulus casting tapes of improved conformability. These casting tapes contain a casting fabric formed of a combination of high modulus yarns and elastomeric yarns. The elastomeric yarns are incorporated into the fabric along the length direction to give the fabric an extensibility of between 40% and 200% in the length direction. Preferably, these fabrics are Raschel Warp Knit fabrics having the elastomeric yarns forming or distributed within the wale yarns. The elastomeric yarns are incorporated into the fabric during the knitting process under a predetermined amount of tension so that the finished fabric gathers or bunches to a moderate degree when it is released from the knitting machine. The resulting fabrics are impregnated with a hardenable prepolymer to provide a casting tape of substantially improved conformability and which has experienced wide-spread commercial success.

Despite the availability of casting tapes of improved conformability, various improvement in strength, cost and the like are still desirable. However, the design of improved casting tapes must be exercised within the limits imposed by various practical constraints. Specifically, improving the strength of a casting tape is typically accomplished by using more high modulus fibers per unit area of the tape. However, this in turn increases the cost of the fabric, increases the stiffness and decreases the conformability. Moreover, fabric processability must be retained in order that the fabric be commercially useful as a practical matter. Thus, the practical constraints involved in casting tape manufacture dictate a trade off between strength and cost, and between conformability and strength, while requiring a good processability.

SUMMARY OF THE INVENTION

The invention provides orthopedic casts and casting tapes which can have improved strength properties and which are highly conformable and/or moldable. Thus orthopedic casts made from tapes of the invention can have strength properties exceeding those of casts made from highly conformable prior art casting tapes having a comparable high modulus fiber content. Nevertheless the moldability, conformability and/or appearance of the casts and tapes of the invention can equal or exceed the comparable prior art casts and tapes. Moreover the tapes and casts of the invention can be produced at a lower cost than highly conformable tapes of the prior art, and do not require modification of commercially available resin systems of the prior art.

The orthopedic casting tape of the invention is provided by the combination of an open mesh fibrous tape and a hardenable liquid resin coated on the fibrous tape. The fibrous tape is a knit fabric having alternating thick and thin portions extending transversely across the tape, i.e. across the tape in the width direction. Although the properties of the tapes and casts are not fully understood, and while not wishing to be bound by theory, it is believed that adjacent thick and thin portions of the tapes of the invention provide separate tape portions that are capable of conforming and flexing with a greater degree of independence from each other than adjacent portions of conventional casting tapes which have a uniform thickness across the width of the tape. It is believed that the thinner sections of the tape may provide a hinge-like function allowing adjacent thicker sections of the tape to conform more precisely to irregular body surfaces and/or to underlying casting tape layers.

In preferred embodiments of the invention, the open mesh fibrous tape is a knit structure defined by a plurality of wales extending longitudinally along the tape and wherein alternating ones or groups of the wales have a thickness when relaxed that is substantially greater than adjacent alternating ones or groups of the wales in the tape. The alternating thick and thin wales provide a ribbed effect or appearance to the tape. Preferably elastic monofilament or multifilament yarns are inlaid into the thicker wales while the thinner wales are free of elastic yarns. It is also preferred that at least the thicker wales include a high modulus fibrous material, such as glass fiber yarns, and that the tape have an extensibility of greater than about 40% in the length direction. Advantageously the knit fabric is a warp knit and also includes high modulus yarns, e.g. glass yarns, as laid in yarns extending in the transverse or width direction of the tape.

Despite the non-uniformity of the tapes of the invention in their width direction, it has been found that casts made from the tapes exhibit an excellent appearance and a high degree of uniformity. In the preferred elastomeric embodiments of the invention which include elastomeric yarns in only a portion of the wales, it has been found that conformability and moldability can equal or exceed the conformability and moldability of the uniform casting tapes now in commercial use which have elastic yarns in all wales of the fabric. Although use of fewer elastomeric filaments can substantially reduce the cost of the tapes, it has been found that there is not an accompanying reduction in functionality and fabric properties. To the contrary, important properties of the tapes and of the finished casts of the invention are comparable or improved significantly.

BRIEF DESCRIPTION OF THE DRAWINGS

In the drawings which form a portion of the original disclosure of the invention.

DETAILED DESCRIPTION OF THE PREFERRED EMBODIMENTS

In the following detailed description, preferred embodiments are discussed in detail to enable practice of the invention. It will be apparent that although specific terms are used to describe the preferred embodiments, these are used in the descriptive sense and not for the purpose of limiting the invention thereto. It will also be apparent that the invention is susceptible to numerous changes as will become apparent from a consideration of the invention as shown in the attached drawings and described below.

The casting tapes of the invention are made from any of various natural and/or synthetic yarns including yarns made from polyesters such as polyethylene terephthalate; polyamides such as nylon 6 and nylon 6, 6; glass; carbon; cotton; rayon; and the like. The term 'yarn' as used herein includes any of various well known yarn structures including yarns formed from monofilament and multifilament continuous filamentary materials, spun yarns formed from staple fibers and the like.

In preferred embodiments, at least a portion of the tape is made from a high modulus yarn. High modulus yarns are known in the art and include high modulus polyethylene terephthalate yarns formed from high intrinsic viscosity (IV) polymer of the type normally used in industrial end uses such as in tires and v-belts; high modulus polyethylene yarns formed from a high IV, high density polymer; fiberglass yarns; polyaramide yarns; and the like. Advantageously, such high modulus yarns have a modulus of elasticity of $8 \times 10^6$ psi or greater.

Figure 1:
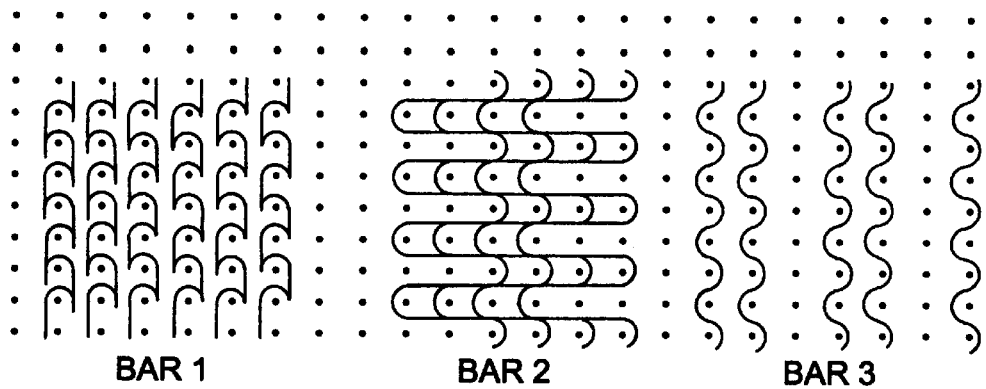
FIG. 1 illustrates the knit notation for one preferred tape embodiment of the invention comprising a three bar Raschel knit in which bar 1 forms simple chain stitch wales and bars 2 and 3 preform lapping motions to lay in yarns and wherein bar 3 lays in elastic filaments in only a portion of the wales of the fabric.
Figure 2:
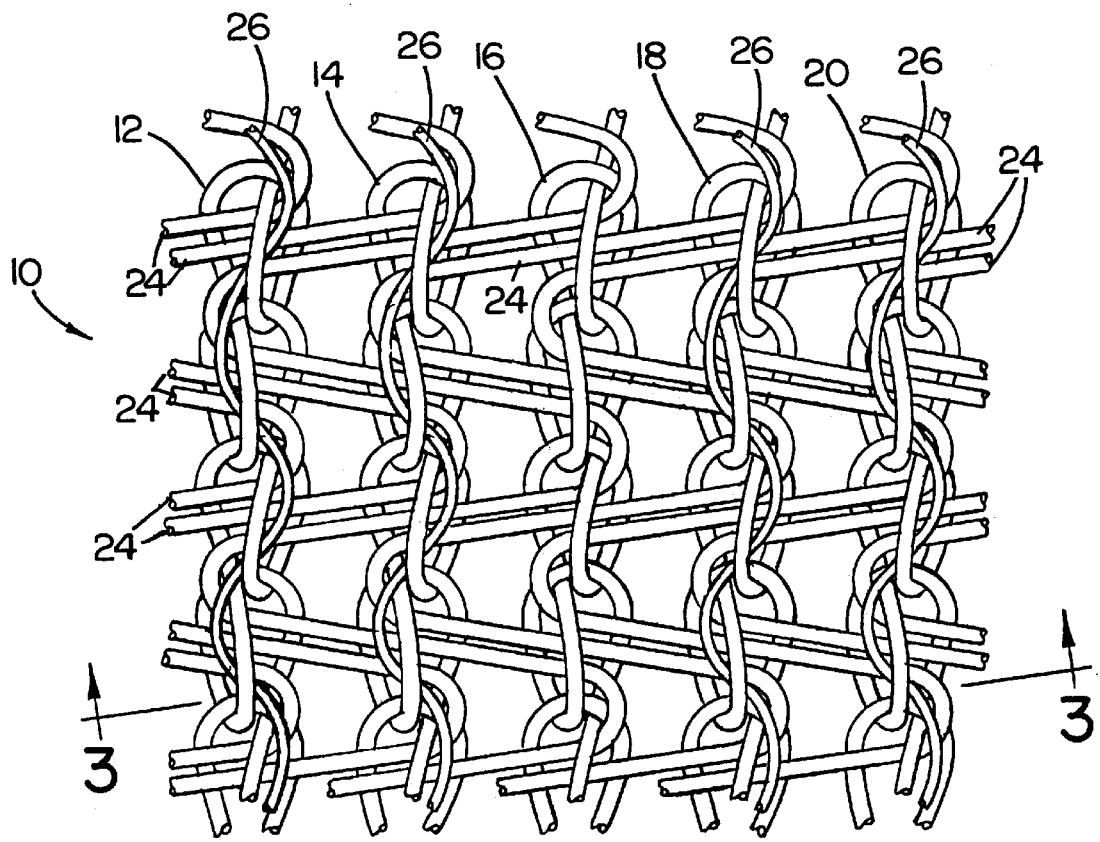
FIG. 2 illustrates a greatly enlarged perspective view of the knit fabric structure formed in accordance with the knit notation of FIG. 1.

FIGS. 1 and 2 illustrate one preferred warp knit construction for casting tapes of the invention. FIG. 1 shows graphically the knit notation for the three bars on a three bar Raschel warp knitting machine used to provide the fabric structure 10 of FIG. 2. Bar 1 uses a stitch notation of 2 0 0 2 to provide a simple chain stitch thereby forming a plurality of wales 12, 14, 16, 18, and 20 as shown in fabric structure 10 of FIG. 2. Bar 2 uses a knit notation of 0 0 6 6 and forms a lapping motion to provide laid in yarns 24 of FIG. 2. Each of bars 1 and 2 use one end (yarn) per needle. Bar 3 uses a knit notation of 0 0 2 2 and also forms a lapping motion to provide laid in yarns 26 of FIG. 2. Bar 3 does not use one end for each needle; instead, two ends are provided for each set of three needles. As a result, wale 16 of fabric 10 does not include a laid in yarn 26 from bar 3.

Preferably, yarns 26 of bar three are elastic extensible yarns, i.e., yarns formed of a structure and/or a material which provides an inherent stretch and recovery. The elastic extensible yarn can be formed of a natural rubber or a synthetic elastomeric polymer such as polyisoprene, polybutadiene, styrene-diene copolymers, copolymers of acrylonitrile and a diene or polychloroprene, copolymers of polychloroprene and other monomers, ethylene-propylene elastomers including ethylene-propylene copolymers and ethylene-propylene-diene terpolymer elastomers, block copolymers of styrene and butadiene or isoprene, polyurethanes such as SPANDEX, and the like.

The elastomeric extensible yarn can alternatively be formed employing a crimped and/or bulked structure employing continuous multifilament yarns made from polyester, nylon, and the like. Improved extensibility can be added to such multifilament yarns by heat treating the knitted tape, after formation thereof, to cause the bulked yarns to contract, thereby adding further extensibility to the yarns and to the fabric.

When elastomeric materials are employed to provide the extensible elastomeric yarn, the elastic fiber component can be wrapped or unwrapped with a material such as cotton, nylon, polyester or the like. Elastomeric filaments may be meltspun or may be a cut thread or filament, i.e., the thread or filament may be cut from a sheet of elastic material such as rubber.

Preferably, the orthopedic tape of the invention has an extensibility of at least about 20%, more preferably between about 40% and about 200%. The stretch characteristics of the fabric can be controlled by selection of the type of yarn, the number of elastic filaments and the denier of the filaments as well as the tension on the elastic filaments during knitting. Preferably, when elastic yarns are employed, the elastic yarns are maintained under a small degree of tension during knitting so that following knitting, the fabric contracts to provide increased extensibility in the final fabric.

Figure 3:
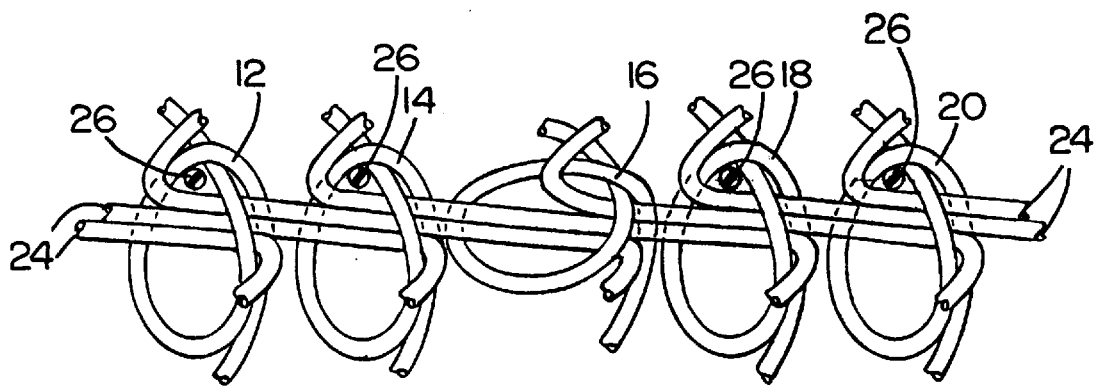
FIG. 3 illustrates an enlarged cross-sectional view of a portion of the fabric of FIG. 2 taken along line 3—3 thereof and illustrates the alternating thicker and thinner sections across the transverse direction of the fabric.

FIG. 3 illustrates a portion of the cross section of the knit fabric structure of FIG. 2, following relaxation thereof. As seen in FIG. 3, each of wales 12, 14, 18 and 20 include laid in filaments 26 from bar 3 as well as laid in filaments 24 from bar 2. Wale 16, on the other hand, includes only laid in yarns 24 from bar 2 and does not include laid in yarn 26 from bar 3. Particularly when high modulus yarns are used to form the wales 12, 14, 18 and 20, the high modulus or stiffness inherent in the yarn causes the yarn to assume a rounded structure, even in the relaxed form illustrated in FIG. 3. The wales 12, 14, 18 and 20 which include an extra filament from bar 3 tend to assume an up-and-down oriented hoop structure, that is, a hoop structure oriented more or less in the "Z" direction of the fabric. Wale 16 which does not include a yarn from bar 3 tends to assume a hoop structure oriented more in the direction of the plane defined by the fabric, i.e., in the X-Y direction. Thus, the fabric illustrated in FIGS. 2 and 3 presents a three-dimensional ribbed appearance because wales 12, 14, 18 and 20 have a greater thickness than wale 16.

The ribbed effect is apparent to the greatest extent when elastomeric filaments are employed as filaments 26 and particularly when high modulus yarns are used for wales 12, 14, 18 and 20. As indicated previously, when elastomeric yarns are used to provide the knit structures, the elastomeric yarn is maintained under tension during the knitting process. Following knitting, the elastomeric yarn relaxes causing the fabric to become gathered. This in turn results in contraction of the wales which include an elastomeric yarn, that is, wales 12, 14, 18 and 20 of FIGS. 2 and 3. Because the wales including the elastomeric yarn becomes gathered, and because the yarns employed to form the wales have a high modulus or stiffness, each gathered wale tends to assume a relatively thick three-dimensional structure. Although the adjacent wales which do not include an elastomeric yarn, i.e., wale 16, are also gathered because of the contraction of the fabric, these wales are free to assume a more planar structure as illustrated in FIG. 3 resulting in a thinner portion of the fabric.

As indicated previously, casts formed from the orthopedic tapes of the invention have been found to typically have a greater strength based on fabric weight. This result is not fully understood and may be due to different factors. As indicated previously, it is believed that the adjacent thick and thin portions in tapes in the invention provide separate tape portions that are capable of conforming and flexing with a greater degree of independence from each other than adjacent portions of conventional casting tapes. This in turn, may provide better surface-to-surface contact between adjacent layers in a finished cast, and/or nesting of the adjacent layers resulting in a greater overall strength for the cast. Alternatively, the loops forming the casting fabric may be oriented in different directions in the final cast, resulting in a hardened cast having greater strength in multiple directions.

It has also been found in accordance with the present invention that the casting tapes having alternating thicker and thinner portions are capable of forming exceptionally strong, hardened structural casts even when the mesh size is outside of the range identified by the prior art as providing strong casting materials. In this regard, U.S. Pat. No. 4,502,479 to Garwood et al. is directed to casting tapes prepared from high modulus fibers and having a mesh size of between 20 and 200 openings per square inch in order to provide finished casts of high breathability and improved strength. The inventors of the present application have found that casts prepared from tapes according to this invention having mesh size openings substantially in excess of 200 openings per square inch have a high degree of strength and breathability despite the teachings of the prior art. Thus in advantageous embodiments of the invention, the tapes have openings in excess of 225 per square inch, and even in excess of 250 per square inch.

Figure 4:
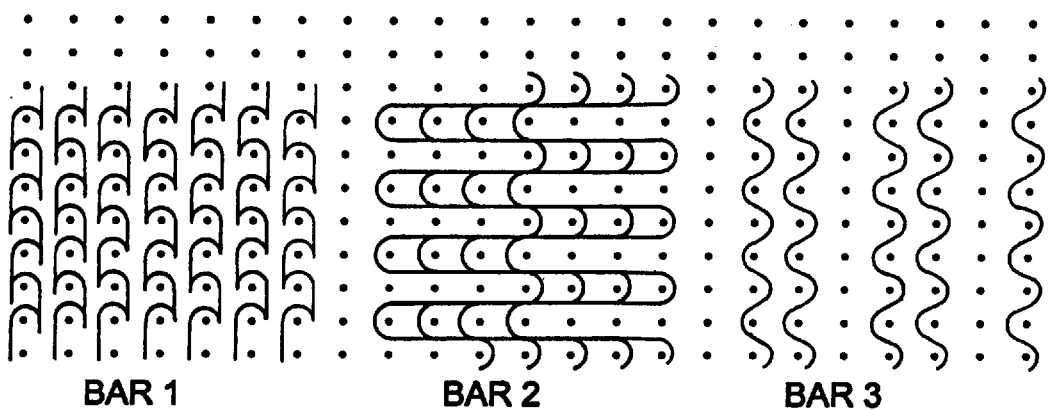
FIGS. 4, 5 and 6 illustrate knit notations for other advantageous knit fabric constructions for orthopedic casting tapes according to the invention.
Figure 5:
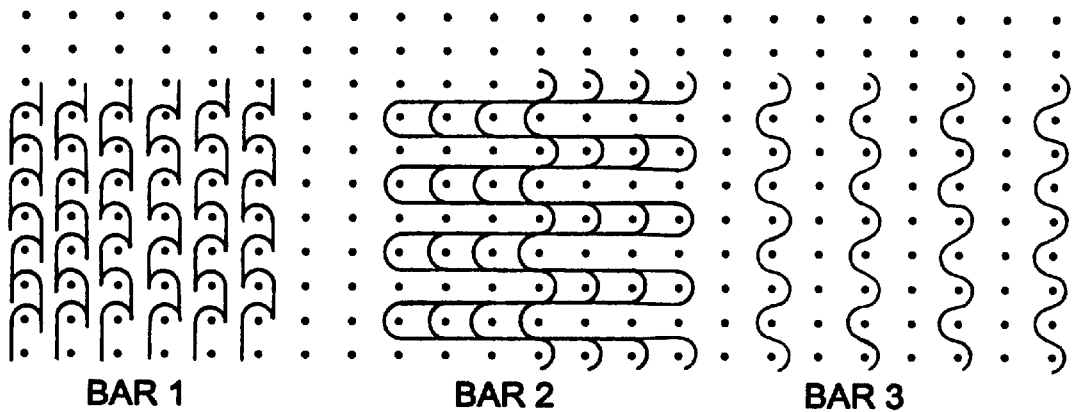
Figure 6:
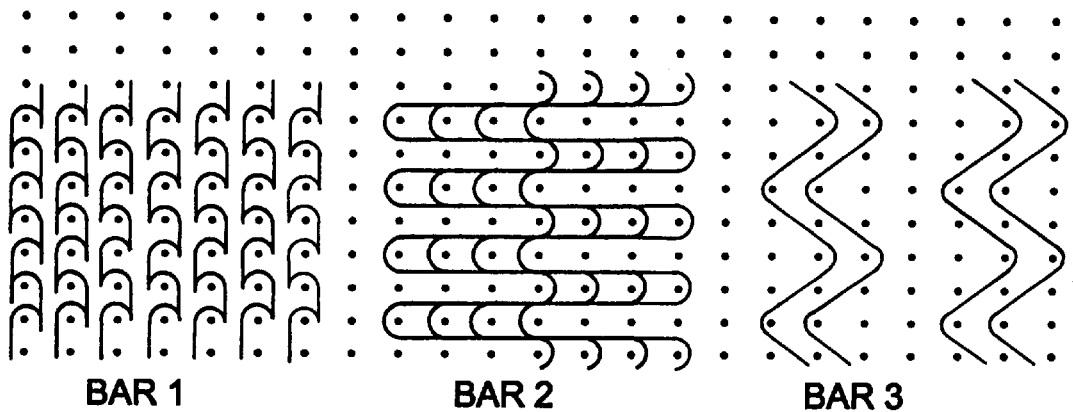

FIGS. 4, 5 and 6 illustrate graphically, knit notations for three bar Raschel knit fabrics for forming casting tapes according to the invention. In FIG. 4, the knit notation for bars 1 and 3 is the same as in FIG. 1. However, the lapping motion of bar 2 is greater than in FIG. 2. In the fabric structure illustrated in FIG. 4, the knit notation for bar 2 is 0 0 8 8. Preferably, the yarns laid in by bar 3 are elastomeric yarns as discussed previously.

In FIG. 5, the fabric has the same structure as in FIG. 1 except that bar 3 lays in yarns on every other needle, rather than on two out of every three needles as in FIG. 1. Again, it is preferred that the yarns laid in by bar 3 are elastomeric yarns.

In FIG. 6, the fabric structure is the same as in FIG. 1 except that the yarns laid in by bar 3 employ the knit notation 2 2 4 4 2 2 0 0. In this case, bar 3 lays in yarns on two adjacent needles for each set of four needles. It will be apparent from FIG. 6 that one wale of each four wales will have a thinner structure due to the yarn of bar 3. It is also contemplated in accordance with the invention that structures similar to FIG. 6 could be modified to produce "thermal knit" type patterns wherein wale thickness varies longitudinally along the wale and wherein thinner portions of such wales are positioned transversely adjacent thicker portions of similar wales.

The orthopedic casting tapes of the invention can be knit on various and numerous knitting apparatus. However, it is preferred that Raschel Warp Knitting apparatus be employed. Preferably, the knitting machine should include 6 to 28 needles per inch and more preferably, should include between 10 and 18 needles per inch, for example, about 14 needles per inch. As disclosed in U.S. Pat. No. 4,668,563 to Buese et. al., which is hereby incorporated by reference, the power of an orthopedic casting bandage is also important. The power should be low to prevent constriction of the patient's limb after the tape is applied to the patient and should be maintained within the range of below 175 grams per inch width based on a fabric stretch of 30%. In the present invention, particularly desirable strength and conformability results have been obtained with casting tapes having a power of between about 20 and about 40 grams, more preferably from about 25 to about 30 grams per inch width at 30% extension.

Following construction of the casting tape, the tape is coated with a hardenable liquid resin capable of curing to form a hardened plastic. Preferably, the hardenable liquid resin is a polyurethane prepolymer which is applied in a dry atmosphere to the fabric by a reverse roll coating or other coating technique known to form cast bandages. The weight of the prepolymer is typically within the range of between about 60 and about 400 grams per square meter, preferably between about 80 and 300 grams per square meter to thereby provide a prepolymer weight between about 30% and 70% by weight, based on the weight of precoated tape. Preferred water curable polyurethane prepolymers for use in this invention are disclosed in Yoon, U.S. Pat. No. 4,433,680, which is hereby incorporated herein by reference.

As indicated previously, in preferred embodiments of this invention, the fabric includes elastomeric yarns in at least a portion of the wales of the fabric. As discussed in the aforementioned U.S. Pat. No. 4,668,563 to Buese which has been incorporated by reference, it is important that the particular elastic thread be compatible with water curable polyurethane prepolymer when employed in the casting tape. Various treatments to ensure compatibility of various elastomeric materials with polyurethane prepolymers may be found in the aforementioned Buese et al. patent.

EXAMPLES 1–12

In the following examples, fabrics were knitted on a Raschel Warp Knitting Machine using glass yarns for bars 1 and 2 as identified below. Bar 3 used, in each case, an acid treated rubber monofilament yarn. The fabric constructions were varied to compare fabric having an elastic yarn for every wale with fabrics having an elastic yarn for only some wales. In each of the fabrics set forth below, the stitch employed on bar 1 was 2 0 0 2. Bar 3, in each case, used the stitch notation 0 0 2 2. Bar 2 was varied among stitch notations of 0 0 8 8 or 0 0 6 6 as set forth in the table below. Properties of the fabric tapes are set forth in Table 1, below. It will be seen that samples 1, 3 and 5 were identical to samples 2, 4 and 6, respectively, except for wale construction. Samples 7, 8, and 9 were roughly comparable to samples 10, 11, and 12.

Casting tapes made from the fabrics set forth below were coated with a polyurethane prepolymer to provide a coating weight of approximately 44–45% as shown in the Table 2, below. Sample weight including prepolymer weight is also reported in Table 2. The samples were then tested by wrapping a sample of approximately 44 inches around a metal dowel having a diameter of 2.75 in. The resultant wrapped tapes were cured and allowed to age for 24 hours. Crush strength was determined using a Chatillon compression tester. The samples were deflected 1 cm. and the load needed to deflect the cylinders determined. With some samples separate tests were preformed at different locations and at different times. These are shown separately in Table 2 below. In addition, the results set forth below are expressed in terms of pounds of force per gram of fabric. This was determined by dividing the crush strength by the coated fabric weight. It can be seen from Table 2 below that the fabrics of the invention had a significantly greater strength per unit weight of fabric (coated) than identical fabrics having a plurality wales of identical thicknesses.

TABLE 1

| Sample | Tape Gauge | Bar 1 Yarn | Bar 2 Yarn | Bar 2 Stitch | Total Wales | Wales with Elastomer | Density g/m$^2$ | Openings per sq. in. |
| --- | --- | --- | --- | --- | --- | --- | --- | --- |
| 1 Comp* | 28 | DE 100 | DE 100 | 0088 | 60 | 60 | 400 | 340 |
| 2 Inv** | 28 | DE 100 | DE 100 | 0088 | 60 | 40 | 344.6 | 287 |
| 3 Comp | 28 | DE 100 | DE 100 | 0066 | 60 | 60 | 330.4 | 292 |
| 4 Inv | 28 | DE 100 | DE 100 | 0066 | 60 | 40 | 301.5 | 268.4 |
| 5 Inv | 28 | DE 100 | F 95 | 0066 | 59 | 40 | 310 | 276 |
| 6 Comp | 28 | DE 100 | F 95 | 0066 | 59 | 59 | 328 | 287 |
| 7 Comp | 24 | DE 75 | DE 100 | 0066 | 54 | 54 | 300 | 236 |
| 8 comp | 24 | DE 100 | DE 100 | 0066 | 54 | 54 | 299 | 268 |
| 9 Comp | 24 | DE 100 | DE 100 | 0088 | 54 | 54 | 302 | 234 |
| 10 Inv | 24 | DE 75 | DE 75 | 0066 | 54 | 28 | 395 | 291 |
| 11 Inv | 24 | DE 75 | F 95 | 0066 | 54 | 28 | 353 | 277.1 |
| 12 Inv | 24 | DE 100 | F 95 | 9966 | 54 | 28 | 317 | 311.3 |

*'Comp' = Comparative Example
**'Inv' = Tape of present Invention

TABLE 2

| Sample | Sample Weight Grams | % Pick-Up | Strength Lbs. Force | Lbs/g F/G |
| --- | --- | --- | --- | --- |
| 1 Comp* Test 1 | 70.17 | 44.98 | 108.25 | 1.54 |
| 1 Comp Test 2 | 67.63 | 45.2 | 100.78 | 1.49 |
| 2 Inv** Test 1 | 61.24 | 44.3 | 109.75 | 1.79 |
| 2 Inv Test 2 | 62.57 | 45.3 | 123.02 | 1.97 |
| 3 Comp Test 1 | 63.47 | 44.52 | 95.0 | 1.50 |
| 3 Comp Test 2 | 62.4 | 44.9 | 87.84 | 1.41 |
| 4 Inv. Test 1 | 58.3 | 43.97 | 108.5 | 1.86 |
| 4 Inv. Test 2 | 57.59 | 44.9 | 105.92 | 1.84 |
| 5 Inv. Test 1 | 58.6 | NR*** | 118.86 | 2.03 |
| 5 Inv. Test 2 | 57.21 | " | 111.91 | 1.96 |
| 6 Comp Test 1 | 60.29 | " | 86.93 | 1.44 |
| 6 Comp Test 2 | 61.4 | " | 93.47 | 1.52 |
| 7 Comp Test 1 | 65.7 | " | 85.45 | 1.30 |
| 7 Comp Test 2 | 65.85 | " | 81.57 | 1.24 |
| 8 Comp Test 1 | 56.82 | " | 71.95 | 1.26 |
| 8 Comp Test 2 | 58.20 | " | 74.79 | 1.29 |
| 9 Comp Test 1 | 58.96 | " | 78.48 | 1.33 |
| 10 Inv. Test 1 | 70.06 | 45.4 | 121.33 | 1.73 |
| 10 Inv. Test 2 | 66.48 | 45.4 | 125.63 | 1.89 |
| 11 Inv. Test 1 | 65.3 | 45.4 | 110.22 | 1.69 |
| 11 Inv. Test 2 | 62.05 | 44.4 | 116.77 | 1.88 |
| 12 Inv. Test 1 | 53.22 | 44.4 | 84.26 | 1.58 |
| 12 Inv. Test 2 | 56.72 | 44.4 | 87.31 | 1.54 |

*'Comp'= Comparative Example
**'Inv' = Tape of this Invention
***'NR' = information not recorded

EXAMPLE 2

In this example, fabric having the structure of Sample 2 in Table 1 above were subjectively evaluated by a small group of casting technicians. The tapes were applied by the casting technicians onto forms representing a human leg and foot. The casting technicians were asked to evaluate the tapes applied on a five step subjective scale ranging from "poor" to "excellent" for properties including "Ease of Application", "Conformability", "Moldability", "Finished Appearance", "Texture" and "Perceived Strength". In addition to casting tapes prepared in accordance with the present invention, the casting technicians were given a commercially available conformable casting tape having the structure of Sample 7 above except that DE 75 glass yarn was used for Bar 2. This commercially available casting tape is known to have a excellent degree of conformability, as well as other excellent properties.

The results of the application of the casting tapes by the test panel resulted in "Ease of Application" ratings for the two groups of tapes which were about the same and in the "excellent" range. "Conformability" ratings were also about the same and were generally considered "excellent". The "moldability" ratings for the casting tapes of this invention were rated closer to "excellent" whereas the commercially available casting tapes were rated closer to "very good". The "finished appearance" of the fabrics of this invention were rated closer to "excellent" while the fabrics of the prior art were rated "very good". The fabrics of this invention were rated as to "texture" as close to "excellent" while the commercially available fabrics were rated closer to "very good". The perceived strength of tapes made using fabrics of this invention were about the same as the commercially available tape, and both were rated close to "very good".

The invention has been described in considerable detail with reference to its preferred embodiments. However, variations and modifications can be made within the spirit and scope of the invention as described in the foregoing detailed specification and defined in the appended claims.

That which is claimed is:

1. An orthopedic casting tape comprising;
an open mesh fibrous tape and a hardenable liquid resin coated onto the fibrous tape, said fibrous tape being a knit tape defined by a plurality of wales extending longitudinally along said fibrous tape, a first plurality of said wales comprising a thickness greater than a second plurality of said wales, and wherein said wales of said first plurality of wales comprising said greater thickness are positioned in alternating relationship to said wales of said second plurality of wales whereby said tape comprises alternating thick and thin portions extending transversely across said tape.

2. The orthopedic casting tape of claim 1 wherein each of said wales having a greater thickness comprises an elastomeric yarn.

3. The orthopedic casting tape of claim 1 wherein each of said thicker wales comprises a high modulus yarn.

4. The orthopedic casting tape of claim 1 wherein said tape has an extensibility greater than about 15 percent in the longitudinal direction.

5. The orthopedic casting tape of claim 4 wherein said tape has an extensibility of greater than about 40 percent in the longitudinal direction.

6. The orthopedic casting tape of claim 1 wherein said knit tape is a Raschel warp knit fabric.

7. The orthopedic casting tape of claim 1 comprising groups of two adjacent thicker wales alternating with individual thinner wales.

8. The orthopedic casting tape of claim 7 wherein each of said thicker wales comprise an elastomeric yarn.

9. The orthopedic casting tape of claim 1 comprising individual thicker wales alternating with individual thinner wales.

10. The orthopedic casting tape of claim 1 wherein said fabric comprises yarns selected from the group consisting of polyester, nylon, and glass.

11. The orthopedic casting tape of claim 1 wherein all of the wales in said knit tape comprise high modulus yarns.

12. The orthopedic casting tape of claim 1 additionally comprising a plurality of laid in high modulus yarns in said knit tape.

13. The orthopedic casting tape of claim 12 wherein each of said wales of greater thickness comprise an elastomeric yarn.

14. The orthopedic casting tape of claim 1 wherein each of said thicker wales include an extensible bulked yarn.

15. The orthopedic casting tape of claim 1 wherein said tape comprises openings of greater than 225 openings per square inch.

16. The orthopedic casting tape of claim 1 wherein said tape comprises openings of greater than 250 openings per square inch.

17. The orthopedic casting tape of claim 1 wherein said tape has an extensibility of greater than about 40% and a power per inch width of tape at 30% elongation of between about 20 and about 40 grams.

18. An orthopedic casting tape comprising;
an open mesh fibrous tape and a hardenable liquid resin coated onto the fibrous tape, said fibrous tape being a knit tape defined by a plurality of wales extending longitudinally along said fibrous tape, a first plurality of wales having a thickness greater than a second plurality of wales, each of said thicker wales comprising an elastic yarn and a high modulus yarn, and wherein said wales of said first plurality of wales having a greater thickness are positioned in alternating relationship to said wales of said second plurality of wales whereby said tape in a relaxed condition comprises alternating thick and thin portions extending transversely across said tape.

19. The orthopedic casting tape of claim 18 wherein said high modulus yarn in said thicker wales comprises glass yarn.

20. The orthopedic casting tape of claim 19 wherein said elastic yarns comprise an elastomeric polymer.

21. The orthopedic casting tape of claim 20 wherein said knit tape has an extensibility of greater than 40 percent.

22. The orthopedic casting tape of claim 21 therein said second portion of wales in said knit tape comprise glass yarns.

23. The orthopedic casting tape of claim 22 wherein said knit tape comprises laid in glass yarns.

* * * * *